(12) United States Patent
Smyth

(10) Patent No.: US 8,202,308 B2
(45) Date of Patent: Jun. 19, 2012

(54) DEPTH COOLING IMPLANT SYSTEM

(75) Inventor: Matthew D. Smyth, St. Louis, MO (US)

(73) Assignee: Matthew D. Smyth, St. Louis, MO (US)

( * ) Notice: Subject to any disclaimer, the term of this patent is extended or adjusted under 35 U.S.C. 154(b) by 917 days.

(21) Appl. No.: 12/164,857

(22) Filed: Jun. 30, 2008

(65) Prior Publication Data

US 2009/0005843 A1    Jan. 1, 2009

Related U.S. Application Data

(60) Provisional application No. 60/947,248, filed on Jun. 29, 2007.

(51) Int. Cl.
*A61F 7/12* (2006.01)
(52) U.S. Cl. .......................... 607/113; 607/96
(58) Field of Classification Search .......... 607/2, 61–63, 607/99, 102, 113, 96
See application file for complete search history.

(56) References Cited

U.S. PATENT DOCUMENTS

| | | | |
|---|---|---|---|
| 4,940,052 A * | 7/1990 | Mann et al. | 607/17 |
| 5,311,876 A | 5/1994 | Olsen et al. | |
| 6,248,126 B1 * | 6/2001 | Lesser et al. | 607/113 |
| 6,506,189 B1 * | 1/2003 | Rittman et al. | 606/41 |
| 6,629,990 B2 * | 10/2003 | Putz et al. | 607/113 |
| 6,648,907 B2 | 11/2003 | Larnard et al. | |
| 6,652,566 B2 | 11/2003 | Larnard et al. | |
| 6,978,183 B2 | 12/2005 | Rothman | |
| 7,004,961 B2 | 2/2006 | Wong et al. | |
| 7,094,234 B1 | 8/2006 | Lennox | |
| 7,156,867 B2 | 1/2007 | Lennox | |
| 2005/0149123 A1 | 7/2005 | Lesser et al. | |
| 2005/0273144 A1 * | 12/2005 | Lennox | 607/105 |

* cited by examiner

*Primary Examiner* — Jackie Ho
*Assistant Examiner* — Leah Stohr
(74) *Attorney, Agent, or Firm* — Polsinelli Shughart PC

(57) ABSTRACT

A depth cooling implant system having a probe device implanted inside a targeted area of the brain, such as the medial temporal lobe, for the treatment of epilepsy is disclosed. The probe device includes a heat pipe having a sensor for detecting the temperature of surrounding brain tissue as well as a plurality of recording electrodes for monitoring EEG activity of the brain. Further, the heat pipe defines a proximal portion in operative engagement with a cooling chip that provides a nearly instantaneous cooling effect to the heating pipe in order to immediately cool the targeted area of the brain when an epileptic seizure is detected. The probe device is operatively associated with a probe controller having a computer and battery arrangement that may be implanted in the patient in order to monitor brain activity and selectively activate the cooling chip for cooling the medial temporal lobe in response to an epileptic seizure.

20 Claims, 3 Drawing Sheets

DEPTH COOLING IMPLANT SYSTEM

CROSS-REFERENCE TO RELATED APPLICATION

This patent application claims priority from U.S. provisional patent application Ser. No. 60/947,248 filed on Jun. 29, 2007 and is herein incorporated by reference in its entirety.

FIELD

This document relates to a depth cooling implant system, and more particularly to a depth cooling implant device for treating a targeted area of the brain.

BACKGROUND

It is estimated that 1% of the entire population suffers from epilepsy. Of those who suffer from epilepsy, approximately 30% do not respond to medicine as a form of treatment. Research has shown that the medial temporal lobe region of the brain is the most common site of origin for epileptic seizures in patients. As such, the surgical removal of the temporal lobe is commonly performed as a treatment for epileptic seizures. However, the surgical removal of the temporal lobe of the brain can also impair language and memory functions of the patient's brain.

Accordingly, there is a need in the art for an effective treatment for epileptic seizures arising from the temporal lobe region of the brain that does not require the surgical removal of the temporal lobe region.

SUMMARY

In an embodiment, a probe device for controlling seizures by cooling brain tissue in a patient may include a heat pipe having a non-insulated end and an opposing insulated end, wherein the non-insulated end of the heat pipe is positioned to contact a targeted region of brain tissue, and a cooling chip in conductive contact with the insulated end of the heat pipe for cooling the insulated end, and wherein transmission of the cooling occurs along the heat pipe to the non-insulated end in order to cool the targeted region of the brain tissue.

In another embodiment, a depth cooling implant system for controlling seizures by cooling brain tissue in a patient may include a probe controller for generating a cooling control signal with the probe controller having a battery for powering the depth cooling implant system; and an implantable probe device operatively coupled to the probe controller, the implantable probe device including a heat pipe having a non-insulated distal portion and an opposing insulated proximal portion, wherein the non-insulated distal portion of the heat pipe is positioned to contact a targeted region of brain tissue; the implantable probe device further including a cooling chip in conductive contact with the insulated proximal portion of the heat pipe, wherein the cooling chip is responsive to the cooling control signal for cooling the insulated proximal portion, and wherein transmission of the cooling occurs along the heat pipe to the non-insulated distal portion to cool the targeted region of brain tissue.

In yet another embodiment, a method for controlling seizures by cooling brain tissue in a patient may include implanting a heat pipe having a non-insulated distal portion and an opposing insulated proximal portion, wherein the non-insulated distal portion of the heat pipe is positioned to contact a targeted region of brain tissue and has a plurality of recording electrodes for detecting electrical brain signals indicative of a seizure event; transmitting a cooling signal to a cooling chip in conductive contact with the insulated proximal portion of the heat pipe, wherein the cooling chip is responsive to the cooling signal for cooling the insulated proximal portion, and wherein transmission of the cooling occurs along the heat pipe to the non-insulated distal portion to cool the targeted region of brain tissue; and implanting a probe controller operatively associated with the plurality of recording electrodes for receiving the electrical brain signals, wherein the probe controller is responsive to the electrical brain signals to record the seizure event and to generate the cooling signal.

Additional objectives, advantages and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the view of the drawings. The headings used in the figures should not be interpreted to limit the scope of the claims.

DETAILED DESCRIPTION

Figure 1:
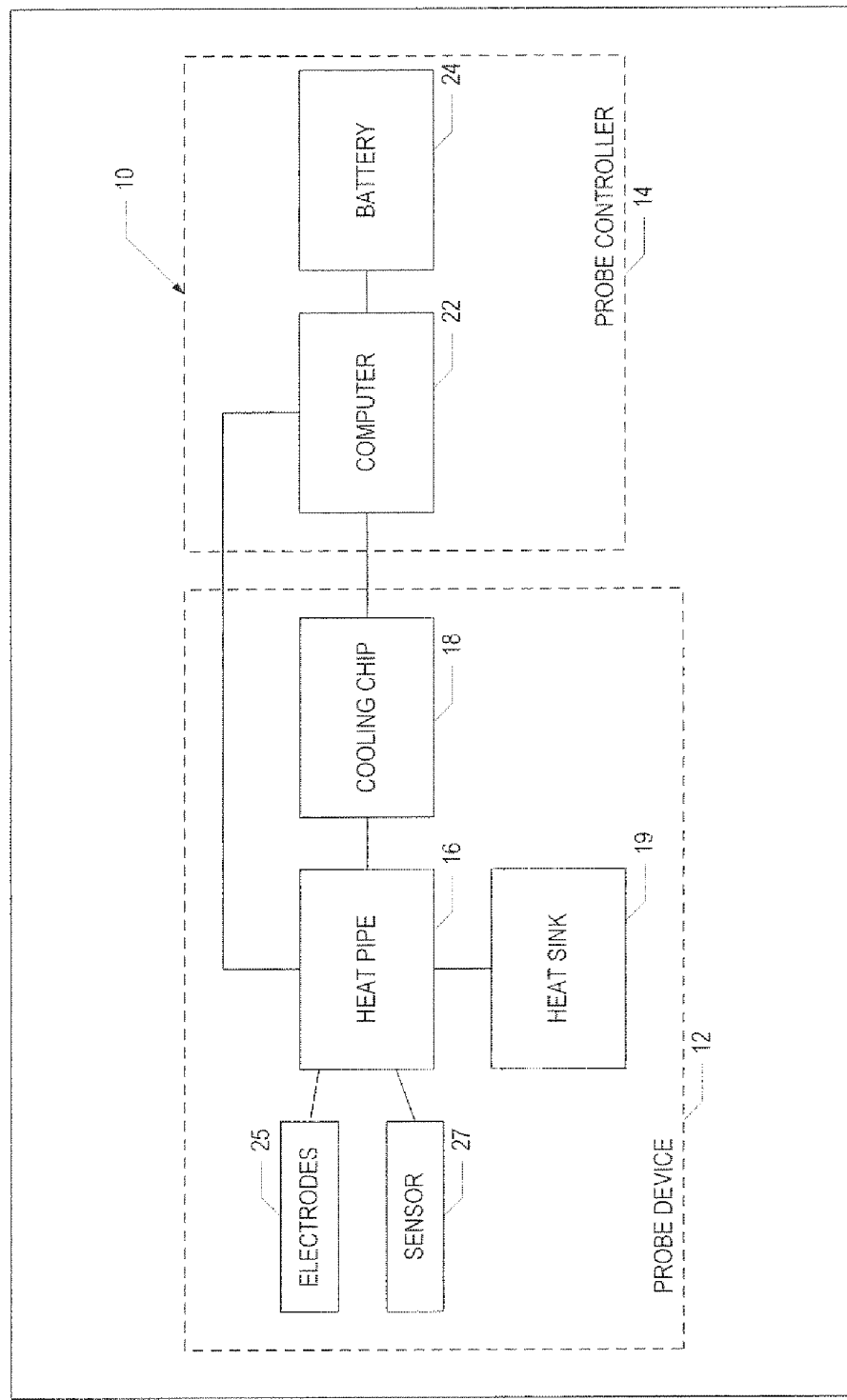
FIG. 1 is a simplified block diagram of a depth cooling implant system.

Referring to the drawings, an embodiment of the depth cooling implant system is illustrated and generally indicated as 10 in FIG. 1. In one embodiment the depth cooling implant system 10 may include a probe device 12 having a heat pipe 16 operatively associated with a cooling chip 18 for providing a cooling effect to a targeted area of the brain when the probe device 12 is implanted inside the cranium 8 of a patient. In addition, the cooling chip 18 is operatively associated with a heat sink 19 for providing a means of dissipating heat generated by the operation of the cooling chip 18. As further shown, the heat pipe 16 and cooling chip 18 are in operative communication with a probe controller 14 for controlling the operation of the depth cooling implant system 10 as shall be discussed in greater detail below.

Figure 2:
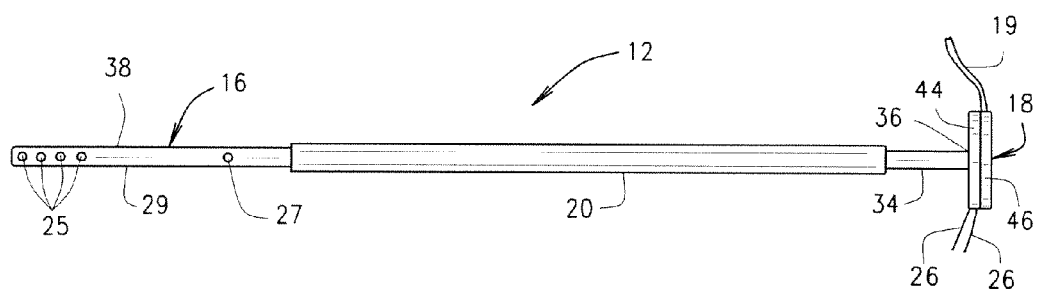
FIG. 2 is a side view of a probe device of the depth cooling implant system.
Figure 3:
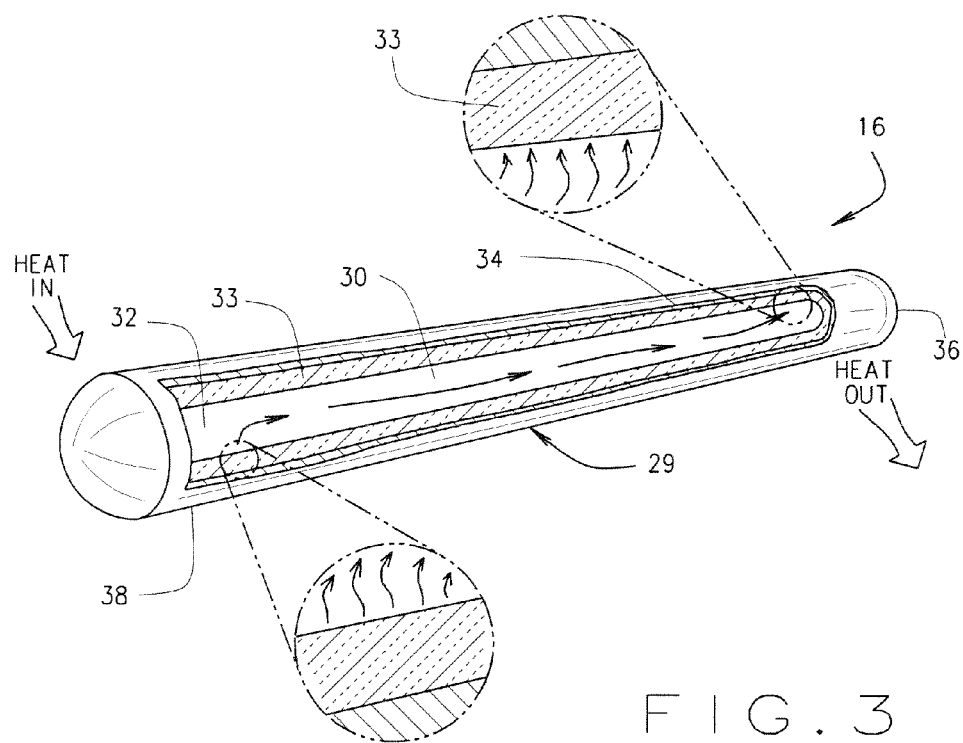
FIG. 3 is a perspective view of a heating pipe for the probe device.

The heat pipe 16 includes a means for providing a cooling effect produced by operation of the cooling chip 18 to be conducted through the heat pipe 16, while permitting heat to be dissipated from the heat pipe 16 in the opposite direction through the heat sink 19. Referring to FIGS. 2 and 3, the heat pipe 16 may include a heat pipe body 29 defining a chamber 32 with an inner tubular member 30 axially disposed therein. The heat pipe body 29 further defines an insulated proximal portion 34 having a proximal tip 36 operatively engaged to the cooling chip 18 and a non-insulated distal portion 38 having a plurality of recording electrodes 25 and a thermocouple sensor 27. The plurality of recording electrodes 25 provide a means for recording EEG brain wave activity when the probe device 12 is implanted inside a targeted area of the brain, while the thermocouple sensor 27 provides temperature data of the surrounding brain tissue around the distal portion 38 of the heat pipe 16.

As further shown, the chamber 32 defined by the heat pipe 16 includes a liquid 33 for conducting the cooling effect provided by the cooling chip 18 from the proximal tip 36 to the distal portion 38 of the heat pipe 16. Conversely, the liquid 33 also permits heat from the distal portion 38 of the heat pipe 16 to be conducted to the proximal portion 34 of the heat pipe 16 for dissipation through the heat sink 19 by the cooling chip 18. In an embodiment, the insulated proximal portion of the heat pipe body 19 may be covered by an insulation tube 20 that insulates the heat pipe 16 from the surrounding brain tissue such that heat may be effectively conducted to the proximal portion 34 of the heat pipe 16 as the cooling effect generated by the cooling chip 18 is conducted to the distal portion 38 of the heat pipe 16. As such, the insulation tube 20 also prevents the cooling effect from being dissipated along the entire length of the heat pipe body 29 while focusing the cooling effect along the distal portion 38 of the heat pipe 16 and the targeted area of the brain. In one embodiment, the target area of the brain may be the medial temporal lobe, although the other areas of the brain are contemplated for the treatment of certain disorders that may benefit from a cooling effect provided by the probe device 12.

As noted above, the probe device 12 is in operative association with a probe controller 14 for providing power and control signals to the probe device 12. Specifically, the probe controller 14 may include a computer 22 for receiving EEG signals representative of brain activity from the recording electrodes 25 and temperature readings of the surrounding brain tissue from the thermocouple sensor 27. The probe controller 14 may also be capable of relaying the EEG and temperature data via telemetry for off-line analysis. The computer 22 may also be capable of analyzing EEG activity and temperature data in order to perform seizure prediction and detection utilizing software algorithms as well as provide control signals to the cooling chip 18 in order to generate the cooling effect to the heat pipe 16. In an embodiment, the computer 22 may be sealed inside a medical grade casing (not shown) that permits implantation of the probe controller 14 inside the body of a patient.

Further, the probe controller 14 may include a battery 24 that provides power to the recording electrodes 25, thermocouple sensor 27 and cooling chip 18. In one embodiment, power from the battery 24 may be supplied to the cooling chip 18 by a closed loop feedback system that activates the cooling chip 18 at predetermined time periods. This closed loop methodology may be a "dumb" system that intermittently activates the cooling chip 18 to provide a cooling effect to the heat pipe 16 in order to prevent epileptic seizures. In the alternative, an open loop feedback system may be used that analyzes the EEG activity transmitted by the recording electrodes 25 and temperature readings from the thermocouple sensor 27 in order to predict seizure activity and provide power to the cooling chip 18 when such a seizure is detected or predicted. This open loop feedback system may also be programmed trancutaneously for a range of temperatures, cycles and cooling periods regardless of the detected EEG activity. In one embodiment, the battery 24 may be a long-term implantable battery or a battery that is capable of being transcutaneously rechargeable by induction or other known recharging technologies.

Referring back to FIG. 2, the probe controller 14 may also include wires 26 that operatively engage the recording electrodes 25 and thermocouple sensor 27 to the computer 22. In addition, the wires 26 may selectively provide power from the battery 24 to the cooling chip 18 when instructed by the computer 22. In one embodiment, the wires 26 may be a compound cable, but other suitable cables or wires for transmitting data or power are contemplated. In an embodiment, the compound cable may be detached from the probe controller 14 and replaced with another compound cable when replacement of wire(s) 26 is required. The wires 26 operatively engaged to the recording electrodes 25 and thermocouple sensor 27 may run between the heat pipe 16 and insulation tube 20 of the probe device 12 and come out near the cooling chip 18. In one embodiment, the wires 26 may run along the compound cable to the probe controller 14, while the wires 26 for powering the cooling chip 18 from the battery 24 may also run along the same compound cable.

As shown, the cooling chip 18 includes a cooling portion 44 for producing a cooling effect to the heat pipe 16 and a warming portion 46 for dissipating heat generated by the heat pipe 16 and the cooling chip 18. The warming portion 46 of the cooling chip 18 is in thermal contact with the heat sink 19 for dissipating heat and allowing for steady state cooling of the cooling chip 18. In one embodiment, the heat sink 19 may be a thermo-conductive baffle implanted under the scalp since the highly vascular nature of the scalp permits a steady blood supply to carry away the heat from the heat sink 19 such that the body of the patient effectively acts as a heat sink.

The cooling chip 18 may be a semi-conductor chip that provides a cooling effect to the targeted area of the brain through the heat pipe 16 when activated by the computer 22. In particular, the cooling chip 18 may be a commercially available Peltier semi-conductor cooling chip that provides near instantaneous cooling effect to the heat pipe 16 when current from the battery 24 is applied to the cooling chip 18 by the computer 22. However, other types of cooling chips 18 suitable for cooling targeted areas of the brain are contemplated.

Figure 4:
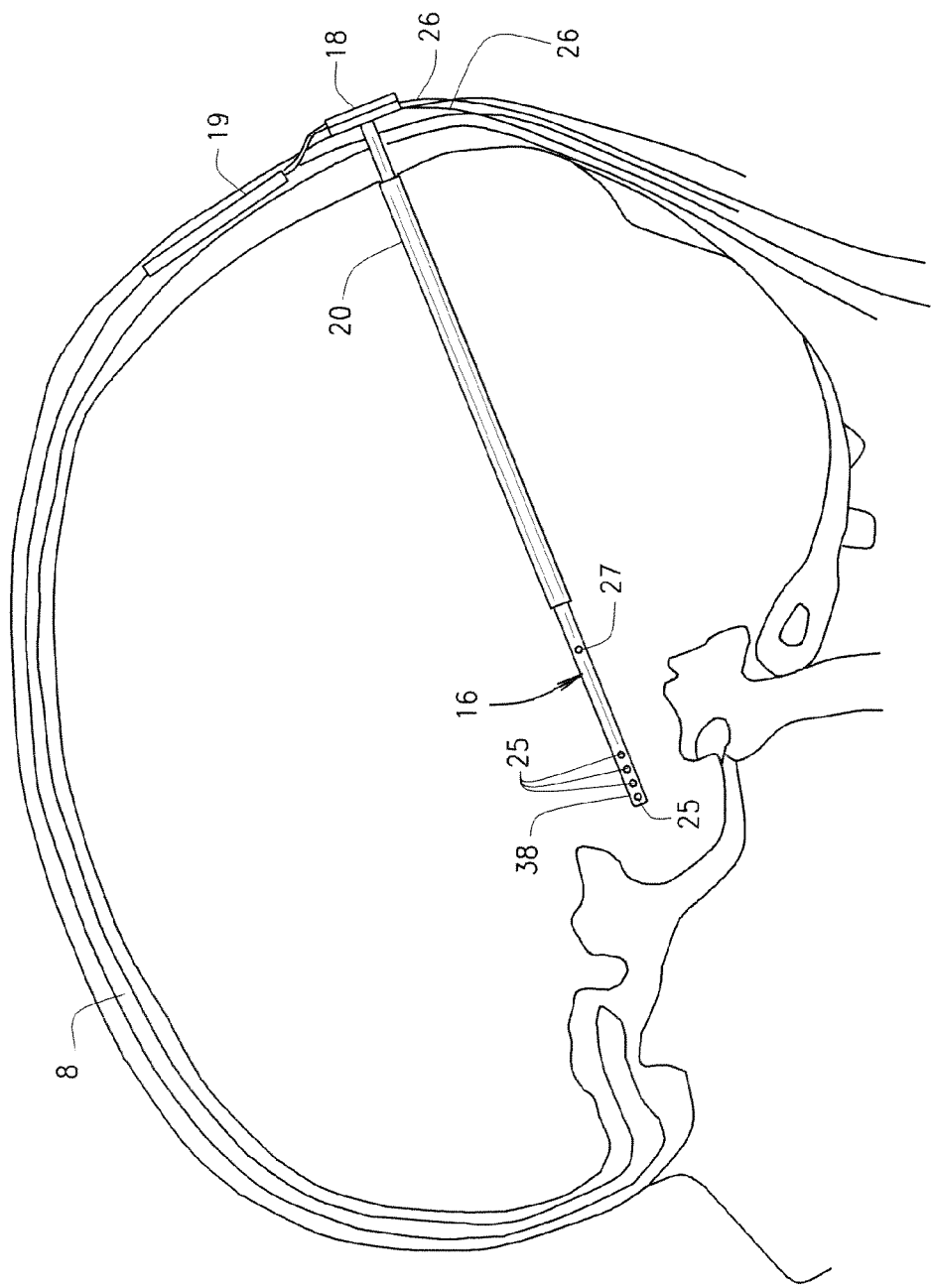
FIG. 4 is a simplified illustration showing the probe device implanted inside the cranium of a patient.

As illustrated in FIG. 4, the heat pipe 16 may be implanted in the medial temporal lobe of the brain, while the heat sink 19 may be implanted under the scalp. In this arrangement, the cooling chip 18 is located outside the cranium 8 when the heat pipe 16 is implanted inside the medial temporal lobe or other targeted areas of the brain.

In one aspect, a method for controlling seizures by cooling brain tissue in a patient may include implanting the heat pipe 16 and probe controller 14 under the scalp of the patient such that the non-insulated distal portion 38 of the heat pipe 16 contacts a targeted region of brain tissue. In this manner, the plurality of electrodes 25 of the heat pipe 16 may detect the electrical brain signals indicative of a seizure event. The method further includes transmitting a cooling signal from the probe controller 14 to the cooling chip 18 for generating a cooling effect that is transmitted to the non-insulated distal portion 38 of the heat pipe 16 to cool the targeted region of the brain tissue. In addition, the probe controller 14 is responsive to brain signals to record a seizure event and generate the cooling signal.

In an embodiment, the heat pipe 16 may have a generally cylindrical configuration, however other suitable configurations are contemplated such as spherical, ellipsoidal, and rectangular configurations. Further, different embodiments of the insulation tube 20 may cover different lengths of heat pipe 16 such that the distal portion 38 of the heat pipe 16 may be uncovered and the proximal portion 34 of the heat pipe 16 covered by the insulation tube 20.

Although the depth cooling implant system 10 may be used for the treatment of epilepsy as discussed above, the depth cooling implant system 10 may have particular application to the treatment of movement disorders as well as neuro-psychiatric applications. In addition, other areas of the brain may be targeted such that the probe device 12 may be implanted to bring a cooling effect to that particular area of the brain.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A probe device for controlling seizures by cooling brain tissue in a patient, the device comprising:
a heat pipe having a non-insulated end and an opposing insulated end, wherein the non-insulated end of the heat pipe is positioned to contact a targeted region of brain tissue; and
a cooling chip in conductive contact with the insulated end of the heat pipe for cooling the insulated end, and wherein transmission of the cooling occurs along the heat pipe to the non-insulated end in order to cool the targeted region of brain tissue, wherein the heat pipe includes a heat pipe body defining a chamber with an inner tubular body axially disposed in the chamber, wherein the heat pipe body defines a proximal portion having a proximal tip operatively engaged to the cooling chip and a distal portion in operative association with a plurality of recording electrodes and a thermocouple sensor, wherein the plurality of electrodes provides a means for recording brain wave activity.

2. A probe device for controlling seizures by cooling brain tissue in a patient, the device comprising:
a heat pipe having a non-insulated end and an opposing insulated end, wherein the non-insulated end of the heat pipe is positioned to contact a targeted region of brain tissue; and
a cooling chip in conductive contact with the insulated end of the heat pipe for cooling the insulated end, and wherein transmission of the cooling occurs along the heat pipe to the non-insulated end in order to cool the targeted region of brain tissue, wherein the heat pipe includes a heat pipe body defining a chamber with an inner tubular body axially disposed in the chamber, wherein the heat pipe body defines a proximal portion having a proximal tip operatively engaged to the cooling chip and a distal portion in operative association with a plurality of recording electrodes and a thermocouple sensor, wherein the thermocouple sensor provides temperature data of the surrounding brain tissue around the distal portion of the heat pipe.

3. The probe device of claim 1, wherein a liquid is disposed inside the chamber for conducting a cooling effect provided by the cooling chip from the proximal portion to the distal portion of the heat pipe.

4. The probe device of claim 1, wherein the cooling chip is in operative association with a heat sink.

5. The probe device of claim 4, wherein the heat sink is a thermo-conductive baffle.

6. The probe device of claim 4, wherein a liquid is disposed inside the chamber for permitting heat from the distal portion of the heat pipe to be conducted to the proximal portion of the heat pipe in order to dissipate the heat through the heat sink.

7. The probe device of claim 1, wherein an insulation tube covers at least a portion of the heat pipe in order to insulate the heat pipe from the surrounding brain tissue.

8. The probe device of claim 1, further including a probe controller in operative association with the probe device for providing power and control signals to the probe device.

9. The probe device of claim 8, wherein the probe controller includes a computer for receiving brain wave signals representative of brain activity.

10. The probe device of claim 8, wherein the computer provides power to the probe device using a closed loop feedback system that activates the cooling chip at predetermined time periods.

11. The probe device of claim 8, wherein the computer provides power to the probe device using an open loop feedback system that predicts seizure activity and provide power to the cooling chip when such a seizure is detected or predicted.

12. The probe device of claim 1, wherein the cooling chip includes a cooling portion for producing a cooling effect to the heat pipe and a warming portion for dissipating heat generated by the heat pipe and the cooling chip.

13. The probe device of claim 11, wherein the warming portion of the cooling chip is in thermal contact with a heat sink for dissipating heat and allowing for steady state cooling of the cooling chip.

14. The probe device of claim 1, wherein the cooling chip is a semi-conductor chip.

15. A depth cooling implant system for controlling seizures by cooling brain tissue in a patient, the system comprising:
a probe controller for generating a cooling control signal;
a battery operatively coupled to the probe controller for powering the probe controller;
an implantable probe device operatively coupled to the probe controller, the implantable probe device comprising:
a heat pipe having a non-insulated distal portion and an opposing insulated proximal portion, wherein the non-insulated distal portion of the heat pipe is positioned to contact a targeted region of brain tissue, wherein the heat pipe includes a heat pipe body defining a chamber with an inner tubular body axially disposed in the chamber; and
a cooling chip in conductive contact with the insulated proximal portion of the heat pipe, wherein the cooling chip is responsive to the cooling control signal for cooling the insulated proximal portion of the heat pipe, and wherein transmission of the cooling occurs along the heat pipe to the non-insulated distal portion of thereof to cool the targeted region of brain tissue, wherein the heat pipe body defines a proximal portion having a proximal tip operatively engaged to the cooling chip and a distal portion in operative association with a plurality of recording electrodes and a thermocouple sensor, wherein the plurality of electrodes provides a means for recording brain wave activity.

16. The depth cooling implant system of claim 15, wherein the probe controller provides power and control signals to the implantable probe device.

17. The depth cooling implant system of claim 15, wherein the probe controller includes a computer for receiving signals representative of brain activity to perform seizure prediction.

18. A method for controlling seizures by cooling brain tissue in a patient comprising:
implanting a heat pipe having a non-insulated distal portion and an opposing insulated proximal portion, wherein the non-insulated distal portion of the heat pipe is positioned to contact a targeted region of brain tissue and has a plurality of recording electrodes for detecting electrical brain signals indicative of a seizure event;
transmitting a cooling signal to a cooling chip in conductive contact with the insulated proximal portion of the heat pipe, wherein the cooling chip is responsive to the cooling signal for cooling the insulated proximal portion, and wherein transmission of the cooling occurs along the heat pipe to the non-insulated distal portion to cool the targeted region of brain tissue, wherein the heat pipe includes a heat pipe body defining a chamber with an inner tubular body axially disposed in the chamber, wherein the heat pipe body defines a proximal portion having a proximal tip operatively engaged to the cooling chip and a distal portion in operative association with a plurality of recording electrodes and a thermocouple sensor, wherein the thermocouple sensor provides temperature data of the surrounding brain tissue around the distal portion of the heat pipe; and implanting a probe controller operatively associated with the plurality of recording electrodes for receiving the electrical brain signals, wherein the probe controller is responsive to the electrical brain signals to record the seizure event and to generate the cooling signal.

19. The method of claim 18, further including a closed loop system that intermittently activates the cooling chip to provide a cooling effect to the heat pipe to prevent seizures.

20. The method of claim 18, further including an open loop system set for a range of temperatures, cycles and/or cooling periods regardless of detected brain activity.

* * * * *